United States Patent [19]

Onopchenko et al.

[11] Patent Number: 4,578,497

[45] Date of Patent: Mar. 25, 1986

[54] TETRAALKYLSILANE SYNTHETIC FLUIDS

[75] Inventors: Anatoli Onopchenko, Monroeville; Edward T. Sabourin, Allison Park, both of Pa.

[73] Assignee: Gulf Research & Development Company, Pittsburgh, Pa.

[21] Appl. No.: 677,047

[22] Filed: Nov. 30, 1984

[51] Int. Cl.$^4$ .............................................. C07F 7/08
[52] U.S. Cl. .................................................... 556/479
[58] Field of Search ......................................... 556/479

[56] References Cited

U.S. PATENT DOCUMENTS

| | | | |
|---|---|---|---|
| 2,721,873 | 10/1955 | Mackenzie et al. | 556/479 X |
| 2,823,218 | 2/1958 | Speier et al. | 556/479 X |
| 2,851,473 | 9/1958 | Wagner et al. | 556/479 X |
| 3,159,662 | 12/1964 | Ashby | 556/479 X |
| 3,220,972 | 11/1965 | Lamoreaux | 556/479 X |
| 3,470,225 | 9/1969 | Knorre et al. | 556/479 X |
| 3,546,266 | 12/1970 | Coffey | 556/479 X |
| 3,658,866 | 4/1972 | Tsuji et al. | 556/479 |
| 3,798,252 | 3/1974 | Nitzsche et al. | 556/479 X |
| 3,814,730 | 6/1974 | Karstedt | 556/479 X |
| 3,865,858 | 2/1975 | Ossko et al. | 556/479 X |
| 3,907,852 | 9/1975 | Oswald et al. | 556/479 X |
| 4,222,951 | 9/1980 | Kreis et al. | 556/479 X |
| 4,292,433 | 9/1981 | Koga et al. | 556/479 |
| 4,292,434 | 9/1981 | Lindner et al. | 556/479 X |
| 4,309,558 | 1/1982 | Koga et al. | 556/479 |
| 4,417,068 | 11/1983 | Kollmeier et al. | 556/479 |

OTHER PUBLICATIONS

Koroleva et al., Zh. Obsch. Khim., 37 (12), 2768, 1967.
Speier, J. L., Advances in Organometallic Chemistry, vol. 17, Academic Press, pp. 407–415, 1979.
Washburne, S. S., "Silicon Compounds Register & Review," Petrarch Systems, Inc., Bristol, PA 19007, p. 10, 1982.
Green et al., J. Chem. Soc. Dalton, 1519–1522, 1977.
Millan et al., J.C.S. Chem. Comm., pp. 673–674, 1981.

Primary Examiner—Paul F. Shaver
Attorney, Agent, or Firm—Roylance, Abrams, Berdo & Goodman

[57] ABSTRACT

Tetraalkylsilane compounds are produced by contacting an admixture comprising
(A) at least one alkylsilane selected from the group consisting of
(i) a monoalkylsilane having the formula R—Si—H$_3$, (ii) a dialkylsilane having the formula R—SiH$_2$—R$_1$, (iii) a trialkylsilane having the formula R—SiH—(R$_1$)$_2$, and mixtures thereof, wherein R and R$_1$ each represent an alkyl radical of from one to 20 carbon atoms per molecule, and
(B) at least one alpha olefin containing from two to about 20 carbon atoms per molecule, under an inert atmosphere with an oxygenated, platinum-containing catalyst in which the platinum catalyst is selected from the group consisting of (i) a platinum catalyst having a basicity substantially equal to or less than that provided by a platinum-containing catalyst having a triphenylphosphine ligand, or (ii) a heterogeneous platinum-containing catalyst, under hydrosilylation conditions. The platinum-containing catalyst can be oxygenated prior to use in the hydrosilylation process or by interrupting the hydrosilylation process and contacting the catalyst with an oxygen-containing gas prior to resuming the hydrosilylation process.

28 Claims, No Drawings

TETRAALKYLSILANE SYNTHETIC FLUIDS

FIELD OF THE INVENTION

The present invention relates to the production of tetraalkylsilane synthetic fluids. More particularly, this invention relates to the production of tetraalkylsubstituted silanes directly from mono-, di- or trialkylsubstituted silanes, or a mixture of such silanes using an oxygenated platinum catalyst.

BACKGROUND INFORMATION

Various synthetic fluids, including synthetic hydrocarbons and silahydrocarbons, have been developed which are useful in the formulation of hydraulic fluids and lubricants which are stable at high temperatures. Tetraalkylsubstituted silanes have been proposed for use in the formulation of hydraulic fluids and lubricants, since they possess excellent viscosities, over a wide temperature range, low pour points and exhibit excellent thermal stabilities.

Various methods have been proposed for synthesizing tetraalkylsilanes involving the addition of a Grignard reagent or alkyllithium compounds to alkyltrichlorosilanes. Such processes are described in U.S. Pat. No. 4,367,343 to Tamborski et al; Rosenberg et al, *J. Org. Chem.*, 1960, Vol. 25, pp. 243-248; and Baum et al, *J. Chem. Eng. Data*, 1961, Vol. 6, No. 1, pp. 142-145.

SUMMARY OF THE INVENTION

It has now been found that tetraalkylsilane compounds can be produced directly from mono-, di- or trialkylsilanes by contacting an admixture of the alkylsilane and an alpha olefin with an oxygenated platinum-containing catalyst under hydrosilylation conditions. More specifically, the process of the present invention comprises contacting an admixture comprising (A) at least one alkylsilane selected from the group consisting of
  (i) a monoalkylsilane having the formula

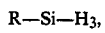
  R—Si—H$_3$, (ii) a dialkylsilane having the formula

  R—SiH$_2$—R$_1$, (iii) a trialkylsilane having the formula

  R—SiH—(R$_1$)$_2$, and mixtures thereof, wherein R and R$_1$ each represent an alkyl radical of from one to 20 carbon atoms per molecule, and
(B) at least one alpha olefin containing from two to about 20 carbon atoms per molecule,
under an inert atmosphere with an oxygenated, platinum-containing catalyst selected from the group consisting of (i) a platinum catalyst having a basicity substantially equal to or less than that provided by a platinum-containing catalyst having a triphenylphosphine ligand, or (ii) a heterogenous platinum-containing catalyst, under hydrosilylation conditions.

It was surprising to discover that tetraalkylsilanes could be produced directly by hydrosilylation of a mono-, di-, or trialkylsilane, since, for example, hydrosilylation of a monoalkylsilane, such as methylsilane, will not produce tetraalkylsilane when the reaction mixture is contacted with a non-oxygenated platinum catalyst. As will be hereinafter demonstrated, the use of a non-oxygenated platinum catalyst in a reaction of a monoalkylsilane and an alpha olefin only provides partial conversion of the monoalkylsilane to form mostly dialkylsubstituted silane and some trialkylsubstituted silane. However, no tetraalkylsubstituted silane was produced and only a portion of the monoalkylsilane is converted. Accordingly, it was completely unexpected that the reaction mixture could be contacted with a catalyst in one step to provide substantially complete conversion to tetraalkylsilane.

The expression "oxygenated platinum catalyst" as used in the present specification and claims means that the platinum catalyst has been contacted with an oxygen-containing gas as to render it active for the hydrosilylation process. Surprisingly, it has been discovered that a reduced platinum catalyst can be rendered highly active for the hydrosilylation process of the present invention by merely contacting the reduced catalyst with an oxygen-containing gas. Such contact may be effected, for example, by bubbling air into the catalyst while in admixture with the olefin used in the hydrosilylation reaction under ambient conditions. Alternatively, the platinum catalyst can be admixed with an inert solvent, such as a paraffinic hydrocarbon, and the air bubbled through the admixture. A still further technique is to run the hydrosilylation reaction with a reduced platinum catalyst, interrupt the reaction, cool the reaction mixture to room temperature, and then bubble an oxygen-containing gas through the reaction mixture to activate the catalyst. The hydrosilylation reaction can then be completed by heating the reaction mixture back up to the reaction temperature.

According to a preferred embodiment of the present invention, the oxygenated platinum-containing catalyst is prepared by contacting the platinum catalyst with oxygen prior to the hydrosilylation reaction.

According to another preferred embodiment of the present invention, the hydrosilylation reaction is conducted with an oxygenated platinum catalyst, and when the catalyst becomes less active for conversion of the alkylsilane, the reaction mixture is cooled, and air is bubbled into contact with the deactivated catalyst to regenerate and reactivate the catalyst prior to continuing the hydrosilylation reaction.

According to still another preferred embodiment of the present invention, a platinum dioxide catalyst is utilized for the hydrosilylation reaction. Although the platinum dioxide catalyst is initially more active for the hydrosilylation reaction, than is a reduced platinum catalyst, the reactivation procedure of the present invention is likewise useful in improving the activity as the catalyst loses activity.

DESCRIPTION OF THE PREFERRED EMBODIMENTS

As previously indicated, the present process involves contacting an admixture comprising
(A) at least one alkylsilane selected from the group consisting of
  (i) a monoalkylsilane having the formula

  R—Si—H$_3$, (ii) a dialkylsilane having the formula

  R—SiH$_2$—R$_1$, (iii) a trialkylsilane having the formula $$R-SiH-(R_1)_2,$$

and mixtures thereof, wherein R and $R_1$ each represent an alkyl radical of from one to 20 carbon atoms per molecule, and (B) at least one alpha olefin containing from two to about 20 carbon atoms per molecule, under an inert atmosphere with an oxygenated, platinum-containing catalyst selected from the group consisting of (i) a platinum catalyst having a basicity substantially equal to or less than that provided by a platinum-containing catalyst having a triphenylphosphine ligand, or (ii) a heterogeneous platinum-containing catalyst, under hydrosilylation conditions.

Preferably, where fluidity at low temperatures is required, the monoalkylsilane is one wherein R is a lower alkyl radical having from one to 4 carbons atoms, with methyl and ethyl groups being especially preferred. Accordingly, the monoalkylsilane may be, for example methylsilane, ethylsilane, propylsilane, n-butylsilane, n-amylsilane, n-hexylsilane, n-heptylsilane, n-octylsilane, n-octadecylsilane, and the like.

Suitable dialkylsilanes include methyloctylsilane, methyldecylsilane, ethyloctylsilane, ethyldecylsilane, methylhexylsilane, butyloctylsilane, hexyloctylsilane, dioctylsilane, didecylsilane, hexyltetradecylsilane, octyldodecylsilane, and the like and mixtures of such dialkyl silanes.

Suitable trialkylsilanes include methyldi(octyl)silane, methyldi(decyl)silane, ethyldi(octyl)silane, methyl(octyl)decylsilane, methyl(hexyl)decylsilane, tri(octyl)silane, tri(decyl)silane, tri(dodecyl)silane, and mixtures of said trialkylsilanes.

The monoalkylsilane is reacted with an alpha olefin having from 2 to about 20 carbon atoms, preferably from 8 to about 14 carbon atoms. The alpha olefin utilized may be a single form of alpha olefin, such as, 1-octene or 1-decene, or may comprise a mixture of alpha olefins, such as, for example, a mixture of 1-octene and 1-decene. If a mixture of alpha olefins is utilized, the relative amounts of alpha olefins may be varied as desired.

Suitable alpha olefins include ethylene, propylene, 1-butene, 1-pentene, 1-hexene, 1-heptene, 1-octene, 1-nonene, 1-decene, 1-dodecene, 1-tetradecene, and the like.

The dialkylsilane and/or trialkylsilane is reacted with an alpha olefin having from 2 to 20 carbon atoms, preferably from 8 to 14 carbon atoms; the alpha olefin utilized may be a single form of alpha olefin, such as, 1-octene or 1-decene, or may comprise a mixture of alpha-olefins, such as, for example, a mixture of 1-octene with 1-decene. If a mixture of alpha-olefins is utilized, the relative amounts of alpha-olefins may be varied as desired.

Any suitable combination of the aforesaid dialkylsilane and or trialkylsilane with the 1-olefin may be utilized. In accordance with a preferred embodiment of the present invention, at least one of the alkyl groups present in the silane represents an alkyl radical of from one to three carbon atoms while the other alkyl groups present in the alkylsilane, the same or different, represent alkyl radicals containing from 8 to 14 carbon atoms each. The reason for this requirement is that a tetraalkylsilane carrying one short and three long alkyl groups will have pour points low enough to be fluid even at −65° F., as needed for operations in the arctic region. When all four alkyl groups on the silicon are long, the product will have higher pour points, and therefore will be fluid only at higher temperatures such as around 0° F. or even higher.

A convenient procedure for conducting the process of the present invention is to form an admixture of the alkylsilane and 1-olefin in a solvent, especially when high molecular reactants are involved. Any suitable solvent can be utilized which is inert under reaction conditions including benzene, toluene, xylene, n-octene, n-decane, or the like. An extraneous solvent is optional however, and excess 1-olefin can be utilized for this purpose, if desired. Next, the platinum-containing catalyst may be admixed with the reactant and utilized as a homogeneous catalyst, or may be provided on a suitable support and incorporated as a heterogenous catalyst.

Any suitable platinum-containing catalyst can be used including chloroplatinic acid, chloroplatinic acid hexahydrate, dichlorobis(triphenylphosphine)platinum (II), cis-dichlorobis(acetonitrile)platinum(II), dicarbonyldichloroplatinum(II), platinum chloride, platinum oxide, and the like. The platinum can be deposited on a support, such as charcoal, alumina, zirconia or the like. Suitable amounts of supported platinum include, for example, from about 0.1 to about 10 weight percent, preferably from about 0.5 to about 5 weight percent based upon elemental platinum. Any platinum catalyst or complex with ligands may be used with the proviso that it have the basicity equal to or less than that provided by triphenylphosphine. For example, hydrosilylation reaction in the presence of dichlorobis(tri-t-butylphosphine)platinum(II) catalyst did not function. While the reason for such behavior is not clear, it appears that t-butylphosphine ligands on the platinum catalyst form complexes which are too stable under the reaction conditions and fail to undergo oxidative addition. Therefore, any ligand on the platinum catalyst that is of higher basicity than that of triphenylphosphine probably will not function as effective hydrosilylation catalyst.

As previously indicated, the platinum catalyst can be in the form of a platinum oxide, namely, platinum dioxide, $PtO_2$. It has been found that the initial activity of platinum dioxide is higher than that of a reduced platinum catalyst for the hydrosilylation reaction.

The activation of the platinum catalyst can be conducted in any suitable manner to contact the catalyst with an oxygen-containing gas. As previously mentioned, the catalyst may be contacted with oxygen-containing gas prior to the hydrosilylation process by bubbling air, for example, through the catalyst in an inert solvent or in the olefin reactant prior to introduction of the silane to saturate the catalyst with air or oxygen. Alternatively, the solid catalyst can be exposed to air. Likewise, the catalyst/solvent or catalyst/olefin admixture can merely be exposed to air for a sufficient long time to enable the air to permeate the admixture and contact the catalyst. Preferably, the oxygen-containing gas is bubbled through the admixture, since contact is more immediate and takes less time. Any suitable contact time may be utilized for bubbling oxygen, for example in the form of air, into the admixture, for example, from about 10 seconds to about 20 minutes, preferably from about 0.25 to about 5 minutes. The appropriate contact time can be easily determined experimentally, and will depend upon the particular catalyst, concentration of oxygen in the oxygen-containing gas, and catalyst concentration. Suitable temperatures include, for example, ambient temperature up to hydrosilylation conversion temperature, for example, from about 0° to about 100° C., preferably from about 20° to about 50° C. If activation is conducted in the presence of a silane, the temperature should be below about 30° C. to avoid reaction of the oxygen with the silane. The amount of oxygen-containing gas required is a very small, catalytic amount, sufficient to activate the catalyst, but insufficient to function as a reactant with the alkylsilane, i.e., a stoichiometric amount. For example, suitable amounts of oxygen include from about one to about 1000 times the amount platinum present on a molar basis, preferably from about 10 to about 800 moles of oxygen per mole of platinum. Greater amounts of oxygen can be used, if desired, without detrimental effects.

Alternatively, the platinum catalyst can be activated after the hydrosilylation reaction has commenced, as indicated by an autogenic increase in temperature since the reaction is usually exothermic. Thereafter, the reaction mixture may be cooled to ambient conditions, and then the oxygen-containing gas bubbled in for sufficient time to activate the catalyst. As indicated, the optimum time for oxygen contact can be easily determined experimentally.

Although it is not intended to limit the present invention by a particular theory or mechanism, it appears that during activation, the upper layer of the catalyst surface interacts with the oxygen to form either platinum-oxygen bonds, or complex oxygen as molecular oxygen, such as $Pt.O_2$.

Any suitable hydrosilylation conditions may be utilized. Suitable temperatures include from about 30° to about 200° C., with from about 50° to about 125° C. being preferred. Suitable pressures include from about one atmosphere to about 35 atmospheres, preferably from about one atmosphere to about 20 atmospheres. The total hydrosilylation residence time is, for example, from about 15 minutes to about 24 hours, preferably from about 30 minutes to about 6 hours. The reaction is conducted under an inert atmosphere by utilizing nitrogen, helium or argon, since the lower molecular weight silanes are pyrophoric in air. Also, the presence of oxygen in stoichiometric quantities produces undesired oxygen-containing condensation products, such as disiloxanes, and etc.

Suitable catalyst concentrations include from about $10^{-6}$ to about $10^{-2}$ mmol of catalyst per mmol of monoalkylsilane, preferably from about $10^{-5}$ to about $10^{-3}$ mmol of catalyst per mmol of silane.

Contact of the catalyst in the reaction mixture with air is preferably made after the monoalkylsilane has undergone from about 20 to about 90, preferably from about 40 to about 80 percent conversion.

Thus, for example, the initial reaction mixture and initial increment of catalyst may be reacted for a period of from about 5 to about 120, preferably from about 15 to about 60 minutes prior to activation with air. In some cases, activation of the catalyst with air prior to its use in a hydrosilylation reaction may be sufficient to convert the silane into tetraalkylsilane, without additional activation.

The reaction process is conducted until a substantial portion of tetraalkylsilane is formed having the formula

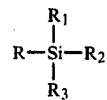

wherein R is an alkyl radical having from one to 20, preferably one to 4 carbon atoms. $R_1$, $R_2$ and $R_3$ are each the same or different alkyl radicals having from about 8 to 20 carbon atoms, preferably from 8 to 14, with the proviso that said tetraalkylsilane contains a total of from 20 to 80 carbon atoms, preferably from 25 to 50 carbon atoms.

Suitable tetraalkylsilanes formed in accordance with the present process include, for example, methyltri(heptyl)silane, methyltri(decyl)silane, methyltri(octyl)silane, methyldi(octyl)decylsilane, hexyltri(octyl)silane, methyldi(octyl)decylsilane, hexyltri(octyl)silane, octyltri(heptyl)silane, ethyltri(octyl)silane, tetra(octyl)silane, hexyltri(tetradecyl)silane, or mixtures of above silanes.

By varying the ratio of 1-octene/1-decene in the feed in a reaction with methylsilane, a mixture of four isomers in the product was expected to be formed in composition depending on the ratio of olefins: methyltri(octyl)silane, methyltri(decyl)silane, methyldi(octyl)decylsilane, and methyldi(decyl)octylsilane.

The process of the present invention is illustrated by the following examples. The hydrosilylation reactions were all conducted under a nitrogen atmosphere. All percentages are by weight unless otherwise indicated.

EXAMPLE 1

An admixture of 10 grams of 1-octene, 10 grams of 1-decene, 1.5 grams of hexylsilane and 0.09 gram of platinum chloride acetonitrile, $PtCl_2(CH_3CN)_2$ in 8 milliliters of toluene was prepared. The mixture was purged with nitrogen for a period of 5 minutes. Next, the mixture was heated under nitrogen until the reaction temperature of 102° C. was reached.

The reaction was continued for a period of 0.5 hour, and then a sample was analyzed. The analysis revealed a product containing 12 weight percent hexylsilane, 78 weight percent dialkylsilane and 10 weight percent trialkylsilane. No tetraalkylsilane was found.

Next, the mixture was cooled to room temperature and was permitted to sit in an open vessel for 16 hours exposed to air. Next, 0.031 gram of platinum chloride acetonitrile catalyst was added, and the system purged with nitrogen for 15 minutes. The reaction mixture was then heated to 105° C. under nitrogen, and after one-half hour, it was found that the reaction was complete. An analysis revealed that the product was 100 percent tetraalkylsilane.

The foregoing tests demonstrate that exposure of the system to air resulted in a highly active catalyst permitting reaction to be taken to completion for production of 100 percent tetraalkylsilane.

EXAMPLE 2

A reaction mixture containing 10 grams of 1-octene, 1.4 grams of hexylsilane, 0.062 gram of chloroplatinic acid, $H_2PtCl_6.6H_2O$, in 6 milliliters of toluene and the admixture was charged to a flask and purged with nitrogen for 15 minutes. The reaction mixture was then heated to 92° C. under nitrogen and analysis of the sample after one hour by gas liquid chromotography (GLC) revealed a product containing 56 weight percent hexylsilane, 39 weight percent dialkylsilane and 5 weight percent trialkylsilane. No tetraalkylsilane was present.

Next, the reaction mixture was cooled to room temperature and permitted to stand in air for 8.5 hours. Then, 0.025 gram of fresh chloroplatinic acid was added to the mixture and the system was purged for 15 minutes with nitrogen and heated to 100° C. under nitrogen. After one hour of reaction, testing revealed that the product was 100 percent tetraalkylsilane.

EXAMPLE 3

A mixture of 10 grams of 1-octene, one gram of hexylsilane and 0.011 gram of chloroplatinic acid was charged to a flask and heated to 85° C. under nitrogen. After one hour under reaction conditions, analysis of a test sample revealed that all of the hexylsilane was converted. The product consisted of 34 weight percent dialkylsilane and 66 weight percent trialkylsilane. The reaction mixture was then cooled to room temperature and saturated with air for 2 minutes by bubbling air through the mixture. Next, the mixture was heated to 98° C. Analysis after one hour revealed that 100 percent tetraalkylsilane was produced.

EXAMPLE 4

A reaction mixture containing 10 grams of 1-decene, one gram of hexylsilane and 0.042 gram of chloroplatinic acid catalyst was saturated with air for one minute at a temperature of 55° C. Heating was continued under nitrogen until the admixture reached a temperature of 106° C. After one hour, analysis revealed that reaction was complete and 100 percent tetraalkylsilane was produced.

EXAMPLE 5

An admixture containing 10 grams of 1-decene, one gram of hexylsilane and 0.032 gram of chloroplatinic acid was charged to a flask and heated to 80° C. under nitrogen. After 15 minutes the mixture consisted of 16 weight percent hexylsilane, 74 weight percent dialkylsilane and 10 weight percent trialkylsilane with no tetraalkylsilane having been formed.

The mixture was then cooled to room temperature and purged with air for 15 seconds before heating the temperature back to a temperature of 98° C. under nitrogen. After 45 minutes, a test sample revealed 22 weight percent trialkylsilane and 78 weight percent tetraalkylsilane. The reaction mixture was cooled once again to room temperature, saturated with air for 15 seconds by bubbling air through the mixture, and then heated to a temperature of 95° C. under nitrogen. After 30 minutes, reaction was complete and tetraalkylsilane was formed as the sole product.

EXAMPLE 6

A reaction mixture was prepared containing 6.7 grams of 1-decene, 0.7 gram of hexylsilane and 0.006 gram of platinum dioxide, $PtO_2$, in a flask and was purged with nitrogen for 5 minutes and heated to 80° C. under a nitrogen atmosphere. After 12 minutes, analysis revealed that all of the hexylsilane was converted and the product consisted of 62 weight percent dialkylsilane and 38 weight percent trialkylsilane.

Next, the temperature was raised to 100° C. under nitrogen and after reacting the mixture for 1.5 hours at this temperature, analysis showed the mixture contained 47 weight percent trialkylsilane and 53 weight percent tetraalkylsilane.

The mixture was then cooled to room temperature and saturated with air by bubbling air through the mixture for a period of 30 seconds. The mixture was then reheated under nitrogen to a temperature of 100° C., and after one hour, analysis revealed that the mixture contained 80 weight percent tetraalkylsilane and 20 weight percent trialkylsilane.

EXAMPLE 7

A reaction mixture was prepared by admixing 510 grams of 1-octene, 210 grams of 1-decene, 130 grams of methyloctylsilane, 60 grams of methyldecylsilane and one gram of a 5 weight percent platinum on charcoal catalyst. The admixture was purged with nitrogen for 15 minutes and then heated under nitrogen to a temperature of 110° C. Analysis of a sample revealed that only partial reaction had taken place. Next, heating was continued under nitrogen to 130° C., and after 3 hours, analysis of a test sample revealed that 29 weight percent of the starting silane remained unreacted.

Next, the mixture was cooled to 25° C. and an additional one gram of the platinum on charcoal catalyst was added. After heating to 130° C. for 5 hours, analysis showed that 13 weight percent of the starting silane remained. The mixture was then cooled and filtered to recover the catalyst. About one-half of the catalyst was saturated with air by bubbling air into admixture of the catalyst with an octane for 10 minutes. The catalyst was then returned to the reaction mixture and the reaction was maintained under a nitrogen atmosphere.

After 2 hours at 130° C., the product was exclusively tetraalkylsilane.

Accordingly, the foregoing examples reveal the requirement that the catalyst be activated with air in order to obtain complete conversion to tetraalkylsilane.

What is claimed is:

1. A process for the production of tetraalkylsilane compounds which comprises contacting an admixture comprising
(A) at leaast one alkylsilane selected from the group consisting of
  (i) a monoalkylsilane having the formula $R-Si-H_3$, (ii) a dialkylsilane having the formula $R-SiH_2-R_1$, (iii) a trialkylsilane having the formula $R-SiH-(R_1)_2$, and mixtures thereof, wherein R and $R_1$ each represent an alkyl radical of from one to 20 carbon atoms per molecule, and
(B) at least one alpha olefin containing from two to about 20 carbon atoms per molecule, under an inert atmosphere with an oxygenated, platinum-containing catalyst selected from the group consisting of
  (i) a platinum catalyst having a basicity substantially equal to or less than that provided by a platinum-containing catalyst having a triphenylphosphine ligand, or (ii) a heterogeneous platinum-containing catalyst, under hydrosilylation conditions, said platinum-containing catalyst having been contacted with an oxygen-containing gas to render it active for the hydrosilylation process.

2. The process of claim 1 wherein said oxygenated platinum-containing catalyst was formed by contacting said platinum-containing catalyst with an oxygen-containing gas prior to subjecting said catalyst to hydrosilylation conditions.

3. The process of claim 2 wherein said platinum catalyst is oxygenated by contact with air while said catalyst is suspended in an inert hydrocarbon solvent.

4. The process of claim 2 wherein said platinum catalyst is oxygenated by contacting said catalyst with air while said catalyst is suspended in said alpha olefin.

5. The process of claim 1 wherein said alkylsilane consists essentially of a monoalkylsilane.

6. The process of claim 1 wherein said alkylsilane consists essentially of an admixture of dialkylsilanes and trialkylsilanes.

7. The process of claim 1 wherein said platinum-containing catalyst is a homogenous catalyst.

8. The process of claim 1 wherein said platinum-containing catalyst is a supported platinum catalyst.

9. A process for the production of tetraalkylsilane compounds which comprises contacting an admixture comprising (A) at least one alkylsilane selected from the group consisting of (i) a monoalkylsilane having the formula

R—Si—H$_3$, (ii) a dialkylsilane having the formula

R—SiH$_2$—R$_1$, (iii) a trialkylsilane having the formula

R—SiH—(R$_1$)$_2$, and mixtures thereof, wherein R and R$_1$ each represent an alkyl radical of from one to 20 carbon atoms per molecule, and (B) at least one alpha olefin containing from two to about 20 carbon atoms per molecule, under an inert atmosphere with an oxygenated, platinum-containing catalyst selected from the group consisting of (i) a platinum catalyst having a basicity substantially equal to or less than that provided by a platinum-containing catalyst having a triphenylphosphine ligand, or (ii) a heterogeneous platinum-containing catalyst, under hydrosilylation conditions, cooling the reaction mixture to room temperature prior to complete conversion of said alkylsilane to a tetraalkylsilane, contacting said catalyst with an oxygen-containing gas, and heating said reaction mixture back to hydrosilylation conditions for substantially complete conversion to a tetraalkylsilane.

10. A process for the production of tetraalkylsilane compounds which comprises contacting an admixture comprising (A) at least one alkylsilane selected from the group consisting of (i) a monoalkylsilane having the formula

R—Si—H$_3$, (ii) a dialkylsilane having the formula

R—SiH$_2$—R$_1$, (iii) a trialkylsilane having the formula

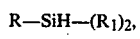
R—SiH—(R$_1$)$_2$, and mixtures thereof, wherein R and R$_1$ each represent an alkyl radical of from one to 20 carbon atoms per molecule, and (B) at least one alpha olefin containing from two to about 20 carbon atoms per molecule, under an inert atmosphere with a platinum-containing catalyst selected from the group consisting of (i) a platinum catalyst having a basicity substantially equal to or less than that provided by a platinum-containing catalyst having a triphenylphosphine ligand, or (ii) a heterogeneous platinum-containing catalyst, under hydrosilylation conditions, and thereafter activating said catalyst by contacting said catalyst with an oxygen-containing gas.

11. A process for the production of tetraalkylsilane compounds which comprises contacting an admixture comprising (A) at least one alkylsilane selected from the group consisting of (i) a monoalkylsilane having the formula

R—Si—H$_3$, (ii) a dialkylsilane having the formula

R—SiH$_2$—R$_1$, (iii) a trialkylsilane having the formula

R—SiH—(R$_1$)$_2$, and mixtures thereof, wherein R and R$_1$ each represent an alkyl radical of from one to 20 carbon atoms per molecule, and (B) at least one alpha olefin containing from two to about 20 carbon atoms per molecule, under an inert atmosphere with a platinum-containing catalyst selected from the group consisting of (i) a platinum catalyst having a basicity substantially equal to or less than that provided by a platinum-containing catalyst having a triphenylphosphine ligand, or (ii) a heterogeneous platinum-containing catalyst, under hydrosilylation conditions, and thereafter activating said catalyst by contacting said catalyst with an oxygen-containing gas, cooling the reaction mixture to ambient conditions, bubbling air into contact with said catalyst, and thereafter heating the reaction mixture until said alkylsilane is substantially completely converted.

12. The process of claim 10 wherein said alpha olefin contains from about 8 to about 14 carbon atoms per molecule.

13. The process of claim 10 wherein said platinum-containing catalyst is a homogenous catalyst.

14. The process of claim 10 wherein said platinum-containing catalyst is a supported platinum catalyst.

15. The process of claim 13 wherein said platinum catalyst is chloroplatinic acid.

16. The process of claim 14 wherein said platinum catalyst is platinum on charcoal.

17. The process of claim 10 wherein said alkylsilane consists essentially of a monoalkylsilane.

18. The process of claim 10 wherein said alkylsilane consists essentially of an admixture of dialkylsilanes and trialkylsilanes.

19. A process for the production of tetraalkylsilane compounds which comprises contacting an admixture comprising
(A) at least one alkylsilane selected from the group consisting of
(i) a monoalkylsilane having the formula R—Si—H$_3$, (ii) a dialkylsilane having the formula R—SiH$_2$—R$_1$, (iii) a trialkylsilane having the formula R—SiH—(R$_1$)$_2$, and mixtures thereof, wherein R and R$_1$ each represent an alkyl radical of from one to 20 carbon atoms per molecule, and
(B) at least one alpha olefin containing from two to about 20 carbon atoms per molecule, under an inert atmosphere with a platinum-containing catalyst selected from the group consisting of (i) a platinum catalyst having a basicity substantially equal to or less than that provided by a platinum-containing catalyst having a triphenylphosphine ligand, or (ii) a heterogeneous platinum-containing catalyst, under hydrosilylation conditions, and thereafter activing said catalyst by contacting said catalyst with an oxygen-containing gas, cooling the reaction mixture to room temperature prior to complete conversion of the alkylsilane, contacting said catalyst with an oxygen-containing gas, thereafter heating said reaction mixture back to hydrosilylation reaction conditions for substantially complete conversion to a tetraalkylsilane.

20. A process for the production of tetraalkylsilane compounds which comprises contacting an admixture comprising
(A) at least one alkylsilane selected from the group consisting of
(i) a monoalkylsilane having the formula R—Si—H$_3$, (ii) a dialkylsilane having the formula R—SiH$_2$—R$_1$, (iii) a trialkylsilane having the formula R—SiH—(R$_1$)$_2$, and mixtures thereof, wherein R and R$_1$ each represent an alkyl radical of from one to 20 carbon atoms per molecule, and
(B) at least one alpha olefin containing from two to about 20 carbon atoms per molecule, under an inert atmosphere with a platinum dioxide catalyst under hydrosilylation conditions.

21. The process of claim 20 wherein said platinum dioxide catalyst is activated prior to hydrosilylation by contact with an oxygen-containing gas.

22. The process of claim 21 wherein said platinum dioxide catalyst is contacted with air while said catalyst is suspended in an inert hydrocarbon solvent.

23. The process of claim 20 wherein said platinum dioxide catalyst is contacted with air while said catalyst is suspended in said alpha olefin.

24. The process of claim 20 wherein said alkylsilane consists essentially of a monoalkylsilane.

25. The process of claim 20 wherein said alkylsilane consists essentially of an admixture of dialkylsilanes and trialkylsilanes.

26. The process of claim 20 wherein said platinum-containing catalyst is a homogenous catalyst.

27. The process of claim 20 wherein said platinum-containing catalyst is a supported platinum catalyst.

28. A process for the production of tetraalkylsilane compounds which comprises contacting an admixture comprising
(A) at least one alkylsilane selected from the group consisting of
(i) a monoalkylsilane having the formula R—Si—H$_3$, (ii) a dialkylsilane having the formula R—SiH$_2$—R$_1$, (iii) a trialkylsilane having the formula R—SiH—(R$_1$)$_2$, and mixtures thereof, wherein R and R$_1$ each represent an alkyl radical of from one to 20 carbon atoms per molecule, and
(B) at least one alpha olefin containing from two to about 20 carbon atoms per molecule, under an inert atmosphere with a platinum dioxide catalyst under hydrosilylation conditions, cooling the reaction mixture to room temperature prior to complete conversion of said alkylsilane, contacting said catalyst with an oxygen-containing gas, and thereafter heating to said reaction mixture back to hydrosilylation reaction conditions for substantially complete conversion to a tetraalkylsilane.

* * * * *